United States Patent [19]

Kerwin

[11] Patent Number: 4,769,019
[45] Date of Patent: Sep. 6, 1988

[54] DRAINAGE APPARATUS

[75] Inventor: Michael J. Kerwin, Ballwin, Mo.

[73] Assignee: Sherwood Medical Company, St. Louis, Mo.

[21] Appl. No.: 14,435

[22] Filed: Feb. 13, 1987

[51] Int. Cl.⁴ .............................................. A61M 1/00
[52] U.S. Cl. .................................. 604/319; 604/323; 137/205
[58] Field of Search ............................... 604/318–323, 604/327, 328, 122; 433/97; 138/145, 146; 137/205

[56] References Cited

U.S. PATENT DOCUMENTS

4,036,231 7/1977 Dodge et al. ............... 128/DIG. 24
4,430,085 2/1984 Ahrens .............................. 604/321

Primary Examiner—C. Fred Rosenbaum
Assistant Examiner—J. L. Kruter
Attorney, Agent, or Firm—Haverstock, Garrett and Roberts

[57] ABSTRACT

A drainage device for draining fluids from the pleural cavity into a collection chamber, the device including a housing having a collection chamber therein and apparatus for supporting a liquid seal chamber in the chamber above the collection chamber. The liquid seal chamber includes a connection to a drainage device in a patient and apparatus enabling visible monitoring of the condition in the liquid seal chamber including at the location where fluids and gases from the patient enter the liquid seal chamber. The device has a novel overflow arrangement for materials to move from the liquid seal chamber into the collection chamber and it has a novel baffle assembly located in the liquid seal chamber to separate the liquid seal chamber into distinct chamber portions.

38 Claims, 4 Drawing Sheets

DRAINAGE APPARATUS

FIELD OF THE INVENTION

This invention relates to drainage apparatus and, more particularly, to a thoracic drainage device for draining fluids from the thoracic or pleural cavity.

BACKGROUND OF THE INVENTION

Thoracic drainage is normally used to remove gases and air as well as blood or other liquids from the pleural cavity surrounding the lungs. Typically, such drainage is needed after chest surgery, after infliction of a chest wound or injury, after a lung puncture or the like, and in some cases simply to remove excessive amounts of fluids that may accumulate as a result of pneumonia or some other sickness condition.

Such thoracic drainage is carried out either under the influence of gravity or by application of a relatively low vacuum sufficient to avoid the possibility of damage to the patient which might occur if a high vacuum were used. One type drainage system that has been long employed is known as a three bottle system, usually glass bottles, wherein one bottle is utilized to collect the body fluids, a second bottle provides an underwater or liquid seal to prevent backflow of the fluids to the patient, and a third bottle is provided to regulate the amount of vacuum that is applied to the pleural cavity by the system.

Various devices have been developed to replace the breakable glass bottles used in past systems and to combine the functions of two or even three of the bottles of the prior system into a more unitary compact system. Among the more useful of such improvement devices are devices with collection units which combine a collection container together with a liquid seal. To avoid the gradual and sometimes excessive buildup of head pressure and the accompanying increased force developed which may be more than safely required to expel the fluids from the pleural cavity, it is usually desired that the liquid seal be maintained at some limited predetermined depth sufficient to protect against surges caused by coughing or sudden pneumothorax, which might otherwise deplete the liquid seal sufficiently to undesirably allow backflow of fluids, gases, solids and semi-solids to the patient. Generally, in drainage devices useful for both gravity and vacuum systems, the liquid seal is confined to a separate container or chamber usually mounted at a somewhat higher elevation than the larger collection chamber. With such an arrangement, however, the water in the liquid seal is subject to being depleted by tipping or falling over of the drainage unit resulting in the loss of the liquid seal and allowing backflow of undesired substances to the patient. One means of attempting to overcome this problem has been to increase the size (or depth) of the liquid seal chamber and thus the volume of fluids it will accommodate while at the same time maintaining a relatively shallow depth of fluid by means of an overflow means. These expedients have disadvantages and for the most part do not establish a liquid seal which can be readily observed and inspected for bubbling and other conditions which are useful for monitoring the breathing of patients on such devices.

The ability to be able to see into and monitor the bubbling in thoracic drainage devices is highly desirable, and considered important in that the visibility of the bubbling through the water seal enables attending medical personnel to be able to readily monitor and evaluate the strength and condition of the patient's respiratory system. Likewise, the visibility of the lower part of a patient's drainage tube which is the part that is connected to a catheter that communicates with the patient's pleural cavity is extremely important. This is because the extent of the "tidaling" that occurs in such tube affords another means of monitoring the patient's respiration especially for conditions of strength and regularity. Tidaling is the rise and fall of liquids in the patient tube in response to changes in pressure in the pleural cavity. Hence, the visibility of the patient drainage or inlet tube to the present drainage apparatus is an additional highly desirable feature.

Of overriding importance in such thoracic drainage devices is a necessity of preserving the integrity of the underwater or liquid seal against the chance of an accidental tipping or knocking over of the entire drainage apparatus which in known devices can place the patient at risk. This is especially true of prior devices that have relatively small volume liquid seals where even small diminution can allow backflow of gases or liquids to a patient. Such accidental tipping or overturning can readily occur in drainage devices that are suspended from bedrails or other means and where the overturned unit is located below the level of the patient, which is necessary for gravity operation. Knockovers can also occur when drainage units are placed on the floor or other flat surfaces below or alongside the patient's bed. Hence, an underwater or liquid seal must be able to preserve its integrity and function properly even during an accident and when rerighted after such.

Also of extreme importance to such drainage devices is their ability to avoid becoming plugged or blocked especially in any of the communicating fluid and gas passages including those passages in the drainage device itself which might become plugged by blood clots or other solids or semi-solids that are drained from the patient's body cavity. Any plugging which prevents easy airflow is likely to rapidly render breathing very difficult for the patient and puts the patient at risk. Furthermore, blockage of the free fluid flow, if prolonged, will result in the backing up of fluids into the patient's body cavity if not checked and corrected in a very timely manner. Consequently, small size, easily blocked passages for the passage of both fluids and gases are to be avoided whenever possible if the utility of a drainage unit for longterm use such as for several hours or even for days is to be realized.

Accordingly, the present invention is concerned with providing a drainage apparatus, and more particularly, a thoracic drainage apparatus which provides the desirable features of maintaining visibility for monitoring bubbling of gases through the water seal portions, and also for monitoring the tidaling of liquid in the patient tube that needs to be observed for checking the patient's respiration. These conditions need to be monitored in order to know the quality and strength of a patient's respiratory system. The present invention also provides means for overcoming the problem of possible loss of the integrity of the underwater or liquid seal as a result of tipping or overturning of the subject apparatus, and the invention reduces the possibility of potential blockage of the fluid and gas passages. The device also includes means to prevent blockage of the liquid seal chamber and the collection chamber associated therewith due to the undesirable buildup of blood clots or other solid or semi-solid materials passing through such passageways. The present invention therefore represents a substantial improvement over known drainage devices, and overcomes many of the disadvantages and shortcomings of devices used for the same or similar purposes.

SUMMARY OF THE INVENTION

The present invention is embodied in a novel thoracic drainage unit provided with a collection chamber adapted to receive fluids and other substances drained from a patient and suitably vented for escape of gases and in some cases for connection to a source of vacuum to assist a weakened patient in breathing. The device also includes a water or fluid seal chamber which is connected to receive body fluid drainage, which seal chamber includes means to maintain a liquid seal which extends above the open lower end of the patient tube, i.e. the tube leading from the patient's pleural cavity, and which also has baffle means in the liquid seal chamber located to direct the incoming fluid drainage, including, the fluids, gases and solid or semi-solid materials that may be drained from the patient's pleural cavity to the collecting chamber. The baffle means are so designed, sized and located as to avoid blockage or plugging of any of the passages or openings in the device and they also play an important roll in maintaining good visibility of the water seal and associated chamber as well as of the lower part of the patient tube which must remain visible for monitoring of tidaling therein. By positioning the liquid for the liquid seal at a convenient highly visible location, the integrity of the device can be easily monitored and maintained and this is true even though solid or semi-solid matter is included in the drainage received from the patient, and even if the drainage unit is accidentally tipped or overturned and subsequently restored to its upright condition.

It is therefore a principal object of the present invention to provide an improved drainage device for accepting drainage from body cavities and the like.

Another object is to provide a drainage apparatus which is safer to use and which has improved means for monitoring critical conditions in the operation thereof.

Another object is to provide a drainage device which is relatively less expensive to construct, and more compact than many known devices used for the same or similar purposes.

Another object is to provide a drainage device that is much less likely than known devices undesirably to backfeed body fluids and gases to a patient.

Another object is to make a patient on a drainage device less vulnerable in the case of an upset of the drainage unit due to carelessness or otherwise.

Another object is to reduce the chance of harming patients on drainage devices.

Another object is to reduce the possibility of clogging the passages and parts in a drainage device due to the presence of solid and semi-solid substances in the materials being drained.

These as well as other objects and advantages of the present invention will become apparent after considering the following detailed description of a preferred embodiment in conjunction with the accompanying drawings.

DESCRIPTION OF THE PREFERRED EMBODIMENT

Figure 1:
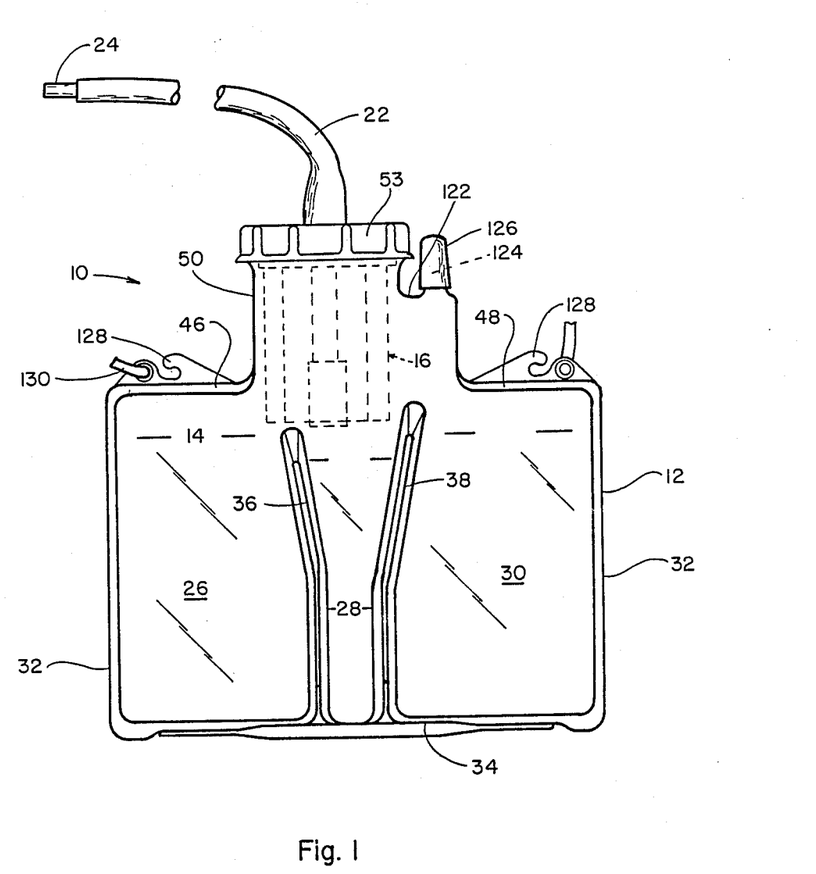
FIG. 1 is a front elevational view of an assembled thoracic drainage unit constructed according to the teachings of the present invention.

Referring to the drawings more particularly by reference numbers, wherein like reference numerals refer to like elements, FIG. 1 shows a thoracic drainage unit 10 preferably constructed of a relatively rigid transparent plastic material or like material in accordance with the present invention. The thoracic drainage unit 10 includes a main collection container 12 having a main three compartment fluid drainage collection chamber 14 and a liquid seal chamber 16 located in an upper portion 50 of the container 12. An inlet fitting 18 is mounted on a wall member 20 which will be described later in connection with a baffle assembly. The wall member 20 closes the upper end of the liquid seal chamber 16 as will also be described. The fitting 18 cooperates with one end of a flexible tube 22, the opposite end of which is connected to one end of a catheter 24 or like drainage device. The catheter 24 is designed to be inserted into the pleural or thoracic cavity of a patient to be drained.

The container 12 is closed on all sides and on the bottom by a bottom wall 34. The container 12 is also divided into three separate chambers 26, 28 and 30, and the container 12 has a peripheral sidewall 32 and spaced intermediate upstanding wall portions or partition walls 36 and 38 which extend upwardly from the bottom wall 34 at the locations shown in FIG. 1. Walls 36 and 38 are preferably formed by partial double wall indentations in the back and front portion of peripheral wall 32, as shown in FIG. 1, said indentations forming a single wall or septum proximating the lateral centerline of container 12. The utility of such indentations will be further described later in connection with alternative stand means.

The partition 36 is somewhat shorter than the partition 38 and both partitions have V-shaped upper edges. This is done so that as the body fluids which first enter the middle portion 28 of the container accumulate, they will eventually overflow into the chamber portion 26 until the fluid depth rises sufficiently that it can overflow into the chamber portion 30 thereby enabling filling of the entire container. This filling action is controlled by the heights of the intermediate wall portions 36 and 38. The container 12 also has spaced upper walls 46 and 48 and an upwardly extending closed wall portion 50 with an opening 52 therethrough for receiving the liquid seal assembly 16. The opening 52 is round and has threads on its outer surface for cooperating with a closure cap 53. All of the walls and partitions of the container 12 are preferably formed integrally and all are preferably of a transparent or transluscent material. The liquid seal assembly 16 and the associated baffle assembly 54 positioned therein are assembled as a unit for inserting into the opening 52 into the upper housing portion 50.

Figure 2:
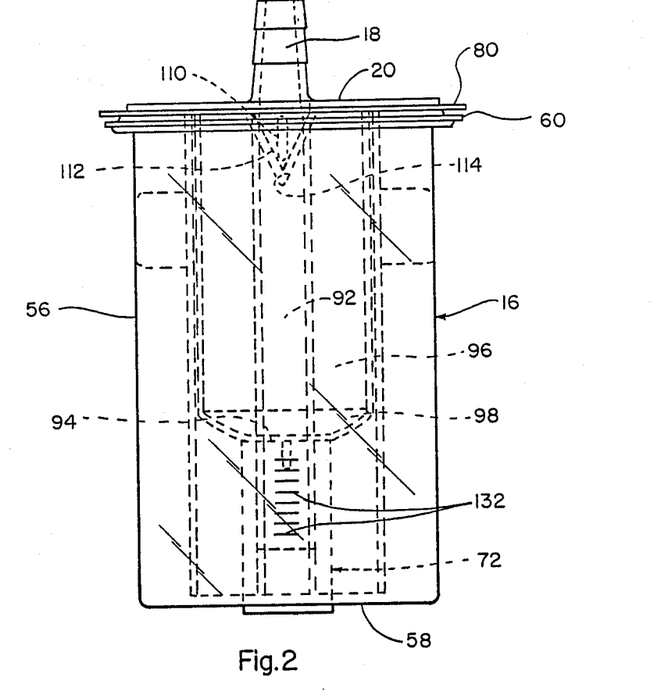
FIG. 2 is a front elevation view of the liquid seal chamber and associated baffle assembly of the drainage unit shown in FIG. 1.
Figure 2A:
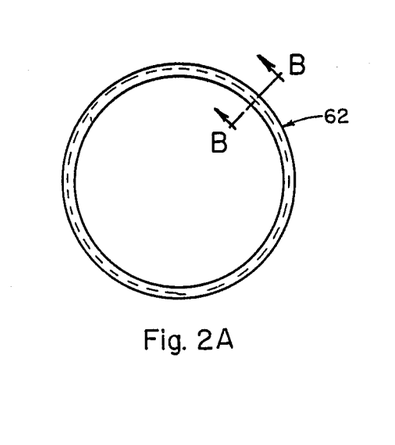
FIG. 2A is a plan view of an elastomeric ring seal around the top perimeter of the liquid seal chamber.
Figure 2B:
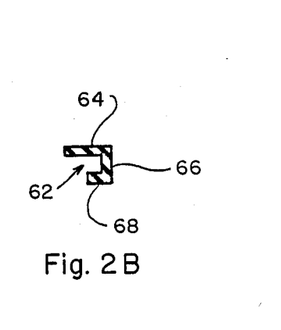
FIG. 2B is an enlarged cross-sectional view taken on line B—B of FIG. 2A.

The details of liquid seal chamber and the associated baffle assembly 54 are important to the invention and are shown in FIGS. 2, 3, 4, 5 and 6. The seal assembly 16 includes a tubular wall 56, open at the top and closed at the bottom by wall 58. The upper edge of the wall 56 has an outwardly extending annular flange 60 which receives an annular gasket 62 (FIGS. 2A and 2B) which fits securely thereon and is formed by annular connected portions 64, 66 and 68 which together embrace the flange 60 and form a seal therewith. The bottom wall 58 of the assembly 16 has a centrally located opening 70 therethrough and a vertical tube 72 is positioned extending through the opening 70 and has a portion 74 that extends upwardly into the chamber 16 and a much shorter portion 76 that extends downwardly from the bottom wall 58 (see FIG. 5).

The baffle assembly 54 extends downwardly into the chamber 16 from the upper closure wall 20 which abuts the upper flange 64 of the seal 62 to seal the chamber 16 closed with the baffle assembly 54 therein. The baffle assembly 54 includes a depending curved wall 82 with spaced parallel wall portions 84 and 86 and curved wall portions 88 and 90 which extend from and connect to opposite sides of a vertical tube 92 that extends downwardly from the wall 20 to a location spaced upwardly from the bottom wall 58, but at a lesser distance from the bottom wall than the upper open end 94 of the tubular member 72. This is important to form a liquid seal in the chamber 16 as will be explained later.

A vertical wall member 96 is attached to the front side of the vertical tube 92, and the wall 96 is wide enough and has its edges beveled to make surface-to-surface contact with the inner surface of the chamber wall 56 when the baffle assembly is inserted therein. The lower end of the wall 96 is connected to a forwardly and downwardly sloping wall 98 which also has its edges shaped to conform to the contour of the inner surface of the wall 56. This is done to establish a liquid free space by and between the walls 96 and 98 and the wall 56. If all of the various walls are made of a clear material such as a clear plastic, it will then be possible for an attendant or other person to see into the subject apparatus and especially into the tube 92 that carries the body fluids and gases being drained from the body cavity into the subject apparatus. The wall 98 is also shown braced to the tube 92 by another wall portion 100.

Figures 3, 4, 5:
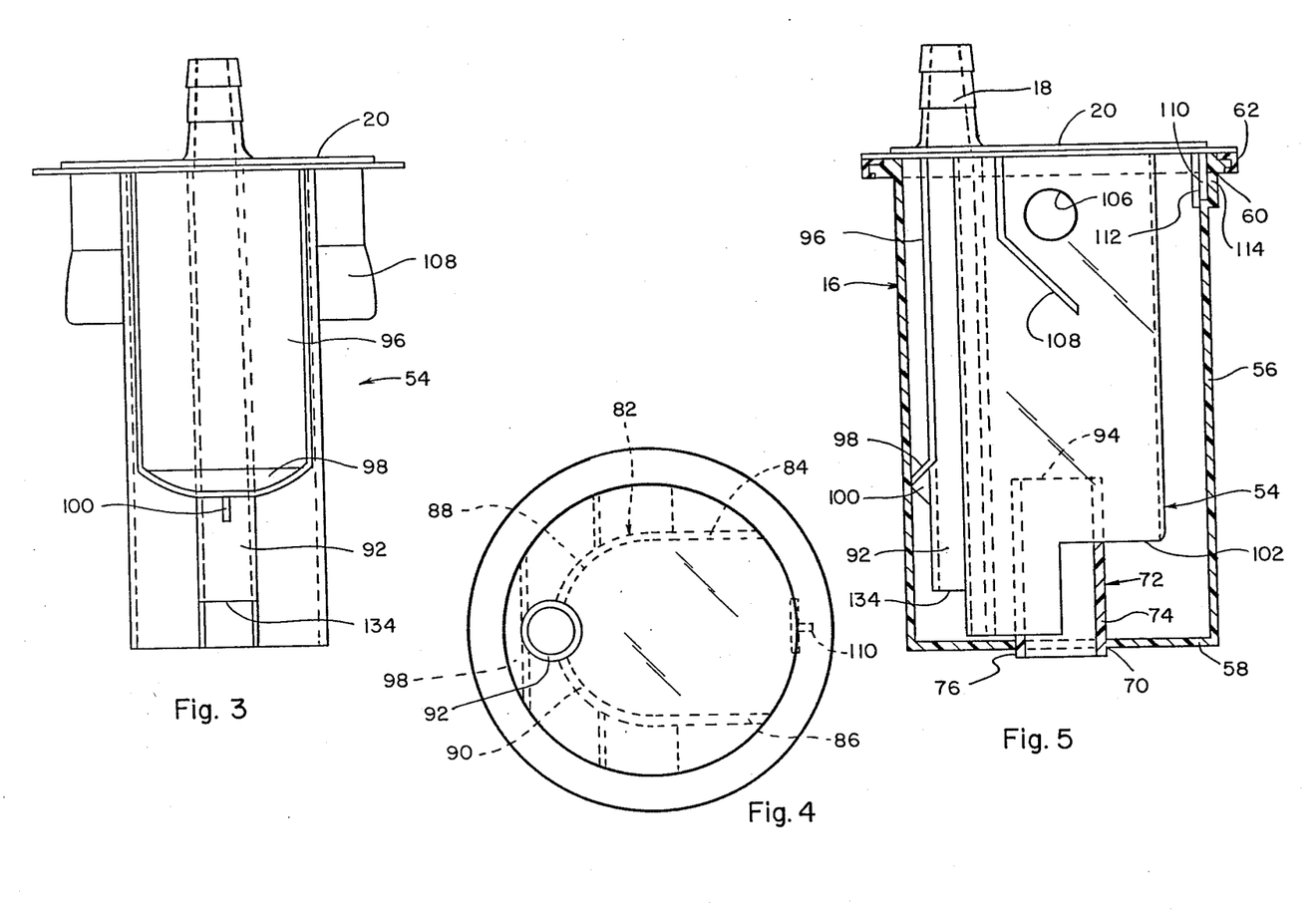
FIG. 3 is a front elevation view of the baffle assembly and associated closure wall with the connection for the patient tube thereon.
FIG. 4 is a top plan view of the baffle and closure wall assembly of FIG. 3.
FIG. 5 is a side elevation view of the baffle and closure wall assembly of FIG. 3 shown positioned in the liquid seal chamber of FIG. 2 which is shown in cross-section.

Referring to FIG. 4, it can be seen that the spaced wall portions 84 and 86 also extend to engage the wall 56 so as to form a substantially enclosed space therewithin. Similar cutouts 102 are formed at the lower rear portions of the wall 84 and 86 at a location below the upper end 94 of the central tube 72 to provide communication to the spaces in the chamber 16 on opposite sides of the wall 82.

Similarly located openings 106 are formed in walls 84 and 86 near the upper ends thereof as shown in FIG. 5, and similar depending V-shaped baffles 108 are mounted on opposite sides of the baffle assembly 54 and extend past the respective openings 106 for engagement with the wall 56. The baffles 108 are provided to deflect any solid and semi-solid substances or foamy liquids that may be present in the chamber 16 should the level of liquids of foams in the liquid seal assembly 16 rise therein to that level. The baffles 108 therefore are located to prevent such substances from entering the openings 106 and clogging or blocking them.

The upper wall 20 of the baffle assembly 54 carries a locating lug 110 which cooperates with a notch 112 in the wall 56 to make it easy to properly locate the baffle assembly 54 therein. In like manner, the chamber housing member 56 carries a triangular shaped lug 114 which cooperates with a locating notch 116 (FIG. 6) in the upper neck portion 52 of the main container 12. The locating lugs and associated notches enable the main container 12, the liquid seal container 16 and the baffle assembly 54 to be quickly and accurately assembled and oriented for use.

The upper wall 20 of the baffle assembly 54 has a tubular fitting 18 which is shaped to sealably cooperate with one end of a flexible tubular conduit 22, the opposite end of which is connected to a device that is inserted into the body cavity to be drained. Several different forms of devices can be used for this purpose.

Figure 6:
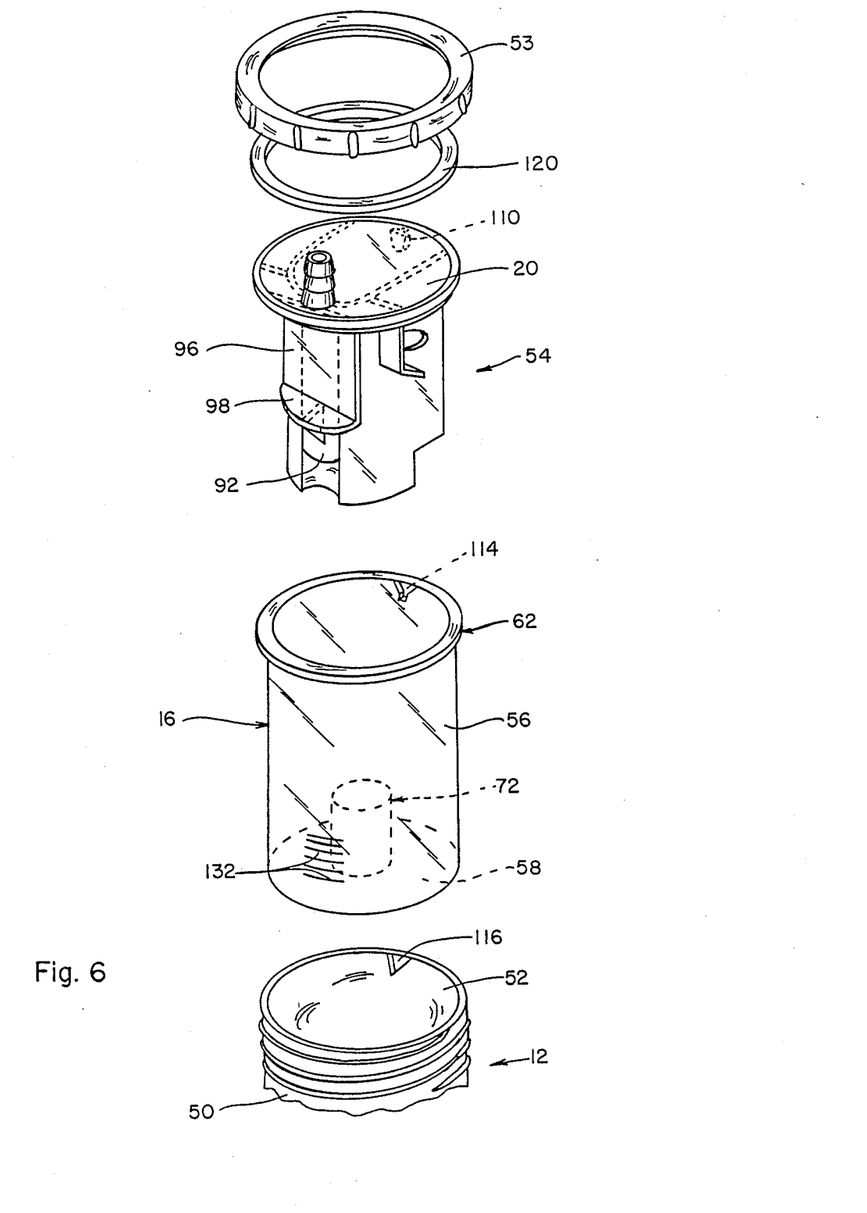
FIG. 6 is an exploded perspective view of the subject drainage unit.

Referring to FIG. 6, it can be seen that the upper portion 50 of the container 12 has the round threaded neck portion 52 which cooperates with the annular threaded closure member 53 which when tightened in place produces a good air-tight seal between the upper wall 20 of the baffle assembly 54 and the sealing ring 62. A gasket such as gasket 120 may optionally be provided in the closure 153 at the location shown in FIG. 6.

The container 12 has another wall portion 122 which has another fitting 124 extending upwardly therefrom. The fitting 124 is shown in FIG. 1 closed by a closure member a cap 126. However, if the cap 126 is removed, a vacuum line (not shown) can be attached to the fitting 124 and used to assist in drawing fluids from the body cavity. Such a connection is usually made to help patients who are in a weakened condition and may need help breathing.

The container 12 also has provisions on its upper surface in the form of hooks 128 and/or a strap 130 for hanging or suspending the device in a convenient location. Alternatively the container 12 can be placed on a flat surface such as the floor or a low stand below the level of the patient with which it is used for drainage. It is convenient and preferable to provide stand means for maintaining the container 12 and assembled device in upright position and to guard against inadvertent upsets of the standing device. Such stand means can take the form of wire supports or flat plastic pieces (not shown) which are conformed to slots or indentations formed in the container 12 by the formation of interior walls 36 and 38. Such slots are shown in FIG. 1 as double walls at the exterior of container 12 with a single wall or septum at the lateral centerline of the container 12. By the provision of the additional stand means the stability of the present device when standing on a flat surface is greatly enhanced.

On the front portion of the wall 56 of the liquid seal chamber 16 are a plurality of spaced scribe lines or like indicia 132. These indicia are shown located in the region of or below the lower forward edge of the wall 98 and provide a visual indication as to the level of liquid in the seal chamber 16. This is important to know since the level of liquid should be maintained high enough to establish the necessary liquid seal taking into account that the lower end 134 of the inlet tube 92 is below the upper open end 94 of the outlet tube 72. The seal and overflow feature is formed by the open ended tube 72 which extends through the bottom wall 58 of the liquid seal chamber 16. This means that liquids can accumulate in the chamber 16 until the level thereof exceeds the height of tube 72 whereupon it overflows into the central chamber portion 28 of the main container 12. The liquid level indicia 132 on the wall 56 provides ready indication as to the depth of the liquid seal in chamber 16.

The lower end of the inlet tube 92 from the patient is foreshortened on the front side so that a space is formed between the lower front edge 134 of the tube 92 and the bottom wall 58 of the chamber 16. This is done to facilitate drainage of the incoming fluids and gases into the chamber 16 and to enable extending the back side of the tube 92 to complete the closure provided by the baffle wall 82. In an actual device the front portions of the tube 92 is shortened by about ⅜ to ½ inch as measured from the bottom wall 58, a distance that is at least as large as the inside diameter of the patient tube 92. The sloping wall 98 is located somewhat above the open lower tube end 134 to prevent incoming fluids from splashing and making it difficult to visually observe the operation through the clear plastic sidewalls.

As described above the rear wall of patient tube 92 is joined to the curved baffle wall 82 and the upper end of the wall 82 is fixed to the lower surface of lid 20. When assembled into the liquid seal chamber 16, the curved wall portions 88 and 90 extend all the way to the bottom wall 58 of the chamber 16 while the parallel baffle walls 84 and 86 terminate well above said bottom wall 58 to provide openings for communication on opposite sides thereof for the substances that are present. The openings 106 near the upper ends of the walls 84 and 86 communicate with the interior of the U-shaped baffle means 82 and serve mainly as outlets for the gases that may be present. This provides expansion space for the gases which space also communicates through the baffle assembly 54 and through the outlet tube 72 to collection chamber 14.

The collection chamber 14 is either vented to the atmosphere in the case of patients who have strong respiratory systems, or connected to suction means as described above. The venting or suction line connection are both made through the open ended fitting 124. To prevent foam or splashing of the drainage fluids and gases from blocking the gas outlet openings 106 in the sidewalls 84 and 86 the baffles 108 are provided. The purpose is to deflect rising substances which may be present in the chamber 16 from reaching and plugging the openings 106. The baffles 108 are located to effectively prevent such blockage. The various edges on the different portions of the baffle assembly 54 are bevelled to closely engage the adjacent surfaces of the member 56 to isolate the various chamber portions from each other but not to seal therebetween as seals are not required between all of the adjacent surfaces for the device to operate. The important thing is to substantially reduce or to prevent the passage or drainage of substances between the various baffle surfaces and the wall 56 and to direct the same to the openings provided therefor in the lower portions of the chamber 16. The relatively close tolerances between adjacent walls will, however, prevent solid and semi-solid substances or foams from moving therebetween.

In use, it has been found desirable to coat the baffle assembly 54 with a medical antifoam solution which when the solvent diluent is evaporated leaves a coating of an effective antifoam agent thereon. This coating acts to reduce or prevent the buildup of foamed liquid at various locations including at or near the gas openings 106, and also serves to prevent persistent foam buildup which might deplete the liquid seal by overflowing through overflow tube 72. A suitable antifoam solution for treating the baffle assembly 54 is a solution of Dow Corning Medical Grade Antifoam A dispersed in a volatile solvent such as a Freon or methylene chloride, a preferred volatile solvent being Freon TF of E. I. Dupont de Nemours and Company. A suitable solution concentration ranges from about 4% to about 10% of the Antifoam A dissolved in from about 90 to about 96% by weight of the volatile solvent such as the preferred Freon TF. The baffle assembly 54 is dipped in this solution until coated up to the lower surface of the cover 20 and the volatile diluent is allowed to flash off, either at ambient conditions or in a low temperature air recirculating oven. The coating of the antifoam agent remaining on the baffle assembly 54 is very effective in preventing the buildup of persistent foam in the liquid seal chamber 16 and this is true even under continuous bubbling of the expired gases through the liquid seal. As noted above the size and extent of such air bubbles which can be viewed in the subject device affords an easily monitored indication of the patient's respiration conditions. The antifoam agent also acts to prevent premature depletion of the liquid seal due to bubbles generated by drainage of a patient pneumothorax or bloody hemorrage which can cause extensive bubbling and persistent foaming in the liquid seal chamber 16.

FIG. 6 shows the manner of assembling the separate portions of the present drainage device. First the liquid seal chamber 16 is seated in the circular neck portion 50 of the container 12, with elastomeric sealing ring 62 in place about its upper edge. Orientation is established by the lug 114 and the notch 116. Thereafter the baffle assembly 54 is positioned in the liquid seal chamber 16 being oriented therein by means of lug 110 and mating notch 112. Finally, the screw cap 53 is threadably tightened over the neck 52 to seal the periphery of lid 20 tightly against the sealing ring 62. The cap 53 also bears on the upper edge of the neck 52 and if desired another sealing ring or gasket 120 can be provided. The flexible conduit 22 can then be attached to the inlet fitting 18 and to a drainage tube for insertion into the patient to be drained.

All parts of the present device are preferably constructed of a transparent and relatively rigid plastic material such as transparent butadiene styrene copolymer, acetate butyrate styrene copolymer or a like substance. When constructed of a relatively rigid plastic material the volumes of the various chambers do not vary substantially even though the pressure inside may vary somewhat due to the patient's respiration or when employing a source of vacuum pressure.

In preparing the present drainage unit for use, the user will precharge sterile water or a saline solution into the liquid seal chamber 16 sufficient to cover the lower opening of patient tube 92. This can be done prior to connecting the unit for use. This can be accomplished by introducing the charged solution via the inlet fitting 18 prior to attaching the drainage unit to the patient's catheter. Preferably, however, it is done through a separate orifice which can be closed by an elastomeric plug, if desired. In practice, the user should charge the liquid seal chamber with about 60 to 85 ml of sterile water or other charging solution prior to use. To maintain sterility charging the solution may be introduced through a separate optional charging orifice (not shown) in the lid 20 which can be closed by an elastomeric plug (not shown). The plug will be reinserted for continued sterility after pouring in the charge.

It has been found that the presently described thoracic drainage unit provides for the effective and relatively long term collection and measurement of fluid drainage from a patient's pleural cavity and it does so with minimal risk to the patient and relatively free from blocking and plugging by blood clots or other solid or semi-solid substances in the fluid drainage. The free flow of the drainage and the liquid seal maintained thereby is further assured by the size and nature of the various passages and parts provided therefor. It can also be seen from the drawings that the exit from the lower end of patient tube 92 is at least as large as the diameter of the same tube and that the passages below the baffle walls 84 and 86 at cut outs 102 as well as opening 94 at the top of the overflow tube 72 are all larger in size then the diameter of tube 92. This means that anything that can enter from the patient should encounter easier passage as it moves through the subject device. Furthermore, no tortuous or convoluted passages are present which might become blocked or plugged by such substances. These features together with the good visibility of the liquid seal in the seal chamber 16 and any fluid tidaling in the patient tube 92, even in the presence of sanguinous fluid drainage from a patient's pleural cavity, provide distinct advantages for the subject thoracic drainage unit.

Furthermore, because of the construction and close fitting relationship of the liquid seal chamber 16 and baffle assembly 54 with patient tube 92 the integrity of the liquid seal is maintained even if the unit is inadvertently overturned so as to not endanger the patient. In tests conducted with the thoracic drainage unit of the present invention a positive liquid seal of at least 1.25 cm depth is maintained despite tipping or overturning of the unit onto the forward wall thereof while essentially no loss at all of the liquid seal is incurred when tipped to either side or backward. In the drainage unit tested the maintenance of a 1.25 cm liquid seal was found to retain its integrity even under tidaling of as much as 60 cm in the patient tube 92 and connecting tube 22. In extended tests the liquid seal retained its integrity in all practical tests.

Under tests of simulated multi-hour drainage and simulated pneumothorax the present thoracic drainage unit performed in a fully satisfactory manner. Gravity drainage was maintained throughout a 72 hour test employing a total of 2500 ml. of sanguinous fluids starting with 500 ml of whole blood followed successively by 500 ml of 75% whole blood and 25% plasma, 500 ml of 50% whole blood and 50% plasma and 1000 ml of 25% whole blood and 75% plasma with a flow rate ranging from an initial rate of 200 ml/hour and diminishing exponentially to 2 ml/hour at 72 hours. Blood clots of up to 1 by 2 cm in area and 3 mm thick were added at intervals during the test. The simulated respiration volume of 6 liters/minute.for half of each 6 second cycle was maintained freely throughout the test. The liquid seal was continuously maintained for the entire period. The addition of blood clots had no apparent effect since no blockage occurred.

Similar excellent results were obtained in a simulated 48 hour mediastinal drainage test under −20 cm H$_2$O vacuum and no air flow, wherein 2500 ml of whole blood was employed at an initial flow rate of 400 ml/hour diminishing exponentially to 0.9 ml/hour. Blood clots of similar size as above described were added at intervals throughout the test with no apparent effect on fluid or air flow rates. The liquid seal was maintained throughout the test at the full 2.4 cm depth. At the end of the test a sudden pneumothorax was simulated by applying vacuum of from 0 to −10 cm H$_2$O. Patient breathing simulated by a positive 5 cm H$_2$O of pressure showed no deterioration in the full 6 liters/minute of air flow obtained in the initial gravity drainage tests. No blockage or increased resistance to fluid flow occurred due to the addition of blood clots.

It should be noted, however, that the flow passage from the upper inlet end or fitting 18 of the inlet tube 92 into and through the space on the outer side of the baffle wall 82 and finally through the cutouts 102 becomes progressively greater. This is important to reduce back pressure which could undesirably cause foaming and backflow.

Thus, there has been shown and described a novel thoracic drainage device which demonstrates all the features and advantages sought therefor. It will be apparent to those skilled in the art after reviewing this description, however, that many changes, modifications, variations and other uses in applications for the subject thoracic drainage device in addition to those which have been disclosed, are possible and contemplated, and all such changes, modifications, variations and other uses and applications which do not depart from the spirit and scope of the invention are deemed to be covered by the invention which is limited only by the claims which follow.

What is claimed is:

1. A drainage device including a main container in which to accumulate substances drained from a patient, said main container having an upright condition with a main chamber portion and a smaller chamber portion thereabove in communication with the main chamber portion, an opening into the smaller chamber portion, a removable assembly for inserting into the smaller chamber portion through the opening including means to maintain the removable assembly in fixed and sealed condition therein, said removable assembly having a closed side wall and a bottom wall connected thereto, a fitting on the removable assembly for attaching to means for inserting into a patient to be drained, said fitting communicating with means forming a tubular passage extending downwardly into the removable assembly to a location spaced upwardly from the bottom wall of the removable assembly, a baffle assembly mounted in the removable assembly, said baffle assembly including the means that form the downwardly extending tubular passage which passage has an upper open end communicating with the fitting and a bottom open end effectively spaced upwardly from said bottom wall, said baffle assembly also including wall means dividing the interior of the removable assembly into distinct chamber portions including first wall means forming a chamber portion on one side of the means forming the downwardly extending passage, and second wall means dividing the rest of the space in the removable assembly into inner and outer chambers, an opening in the bottom wall of the removable assembly in communication with the inner chamber portion and an open ended tube positioned in said opening and extending upwardly from the bottom wall to an upper open end located in the removable assembly at a greater elevation than the effective elevation of the lower end of the means forming the tubular passage.

2. The drainage device of claim 1 wherein the height of said open ended tube positioned in said opening maintains a minimum fluid depth in the removable assembly that is greater than the elevation of the lower end of the means forming the tubular passage.

3. The drainage device of claim 1 wherein said main container has gas outlet means located near the top thereof to permit gases contained therein to escape.

4. The drainage device of claim 3 wherein when said device is in operation said means forming a tubular passage extends downwardly into said removable assembly to below the level of liquid maintained therein such that gases and fluids drained from the patient must pass through at least some of the liquid contained in said removable assembly to reach the open ended tubular member and pass into the main chamber portion.

5. The drainage device of claim 1 wherein said second baffle wall means has at least one opening therethrough located adjacent to the upper end thereof for communicating the inner and outer chamber portions on opposite sides thereof.

6. The drainage device of claim 1 wherein said means to maintain the removable assembly in fixed and sealed condition in the smaller chamber portion includes an elastomeric sealing means mounted on the baffle assembly and a closure cap engageable with the main container and with the sealing means.

7. The drainage device of claim 1 wherein said main container, said smaller chamber portion, said removable assembly and said baffle assembly are all formed from relatively rigid transparent plastic material.

8. The drainage device of claim 1 wherein said smaller chamber portion and said removable assembly positioned therein include cooperatively engageable means located to predeterminedly orient said removable assembly in the main container with the tubular passage means at a location to be easily observed visually.

9. The drainage device of claim 1 including indicia means on the removable assembly adjacent to the effective lower end of the downwardly extending tubular passage to provide a visual indication as to the condition of the materials being collected therein.

10. A drainage device for collecting drainage from a body cavity of a patient comprising a relatively rigid transparent container having a fluid drainage collection chamber therein, means forming a liquid seal chamber disposed in the upper portion of said container, said liquid seal chamber having a side wall closed at one end by a bottom wall, an upper wall and overflow means in said bottom wall for communicating the liquid seal chamber with the collection chamber, said overflow means including an open ended tubular member extending upwardly from the bottom wall into the liquid seal chamber a predetermined distance to establish outlet from the liquid seal chamber into the transparent container through which liquids and gases contained therein can pass, a fitting on the liquid seal chamber for coupling to a drainage instrument to be inserted into a patient, fluid passage means communicating with the fitting at the upper end thereof and extending downwardly into the liquid seal chamber to within a predetermined distance from the bottom wall thereof, said predetermined distance being less than the distance from the bottom wall to the upper open end of the tubular member so that all liquids and gases entering the liquid seal chamber from the patient must pass through some liquid contained in the liquid seal chamber in going through the liquid seal chamber and from there into the collection chamber, and a baffle assembly positioned in the means forming the liquid seal chamber including first baffle means isolating a portion of the liquid seal chamber on one side of the fluid passage means to prevent substances and bubbles in the liquid seal chamber from interfering with the visibility of the fluid passage means, and second baffle means dividing the interior of the liquid seal chamber into separate inner and outer chamber portions, the inner chamber portion communicating with the open ended tubular overflow member, said second baffle means having a foreshortened portion at the lower end thereof to provide limited communication between the inner and outer chamber portions.

11. The drainage device of claim 10 wherein said means forming the liquid seal chamber and said baffle assembly including the fluid passage means are formed of a relatively rigid moldable transparent plastic material.

12. The drainage device of claim 10 including closure means for sealably retaining said means forming the liquid seal chamber and associated baffle assembly in the upper portion of the transparent container.

13. The drainage device of claim 12 wherein said closure means includes a screw cap and means on the transparent container threadably engageable therewith.

14. The drainage device of claim 13 wherein the means forming the liquid seal chamber has a annular flange with an elastomeric annular seal mounted thereon in position to be sealably engaged by the threaded screw cap.

15. The drainage device of claim 10 wherein the first and second baffle means and the fluid passage means are constructed as a one piece unit.

16. The drainage device of claim 10 wherein said means forming the liquid seal chamber is cylindrical in shape.

17. The drainage device of claim 10 wherein said open ended overflow tubular member is centered in the bottom wall of the means forming the liquid seal chamber.

18. The drainage device of claim 10 including indicia lines on the means forming the liquid seal chamber in position to indicate the level of liquid contained in said liquid seal chamber.

19. The drainage device of claim 10 including cooperatively engageable means on the transparent container and on the means forming the liquid seal chamber to predeterminedly orient the means forming the liquid seal chamber in the transparent container.

20. The drainage device of claim 10 including cooperatively engageable means on said means forming the liquid seal chamber and on said baffle assembly to predeterminedly orient said baffle assembly in said means forming the liquid seal chamber.

21. The drainage device of claim 10 wherein said fluid passage means and first baffle means are oriented near one side of said transparent container so as to be easily visible.

22. The drainage device of claim 10 wherein the collection chamber is divided into a plurality of separate communicating chamber compartments including at least one partition wall extending inwardly a predetermined distance from the bottom thereof.

23. The drainage device of claim 10 wherein said second baffle means includes a second opening in the upper wall thereof communicating the inner and outer chamber portions on opposite sides thereof, said baffle assembly having a third baffle means in position below the said second opening to deflect solid and semi-solid substances rising in said liquid seal chamber to prevent them from entering said second opening.

24. The drainage device of claim 10 wherein said container includes means for supporting the device in a suspended condition.

25. A drainage device for collecting drainage from a body cavity of a patient comprising a container having a fluid drainage collection chamber therein, means forming a liquid seal chamber disposed in the upper portion of said container, said liquid seal chamber having sidewall closed at one end by a bottom wall, separate lid means therefor and overflow means in said bottom wall for communication with the collection chamber, said overflow means including an open ended tubular member extending upwardly from the bottom wall into the liquid seal chamber a predetermined distance, said liquid seal chamber adapted to contain a sealing liquid therein, fluid passage means into said liquid seal chamber, means connecting said fluid passage means in communication with a cavity of a patient to be drained, said passage means having a lower open end spaced upwardly from the bottom wall of said seal chamber such that when said device is in operation body fluids and gases from said cavity flow through the passage means and out the open lower end thereof into the liquid seal chamber, the liquid seal chamber being capable of being charged with a sealing liquid that extends above the lower open end of the pasage means which is at a lower level than the upper end of the open ended tubular member of the overflow means, baffle means positioned in the liquid seal chamber in abutment with the sidewall of said liquid seal chamber dividing the liquid seal chamber on opposite sides thereof into inner and outer chamber portions, the passage means communicating with the outer chamber portion, and vertically spaced openings formed in the baffle means communicating the inner and outer chambers, said openings being spaced laterally in the liquid seal chamber from the passage means.

26. The drainage device of claim 25 wherein said container, said liquid seal chamber and said baffle means including the lid means and the passage means are formed of a relatively rigid moldable transparent plastic.

27. The drainage device of claim 25 including means sealably retaining the means forming the liquid seal chamber and associated baffle assembly in said container.

28. The drainage device of claim 27 wherein said closure means includes a screw cap and means on the container threadedly engageable therewith.

29. The drainage device of claim 27 wherein said sealable retaining means includes means forming a seal between the lid means, the baffle assembly and the container.

30. The drainage device of claim 29 wherein said sealable retaining means comprises an elastomeric seal.

31. The drainage device of claim 25 wherein said overflow means is centered in the bottom wall of said liquid seal chamber.

32. The drainage device of claim 25 including indicia means on the wall of the means forming the liquid seal chamber at a location adjacent to the lower open end of the fluid passage means.

33. A body fluid drainage device comprising a container including a drainage collection chamber in a lower portion thereof, and means forming a removable liquid seal chamber above and extending downwardly into said collection chamber, said liquid seal chamber including a closed sidewall and a bottom wall separating the collection chamber and the liquid seal chamber, a first passage means extending through said bottom wall and open at the upper and lower ends thereof, said first passage means extending upwardly a predetermined distance above said bottom wall, and second passage means for fluid communication with a patient and extending downwardly in the liquid seal chamber to a location below the upper end of the first passageway means, the first passage means having a larger cross-section than the second passage means.

34. The body drainage device of claim 33 wherein the upper end of the second passage means is of smaller cross-section than the lower end thereof.

35. A body fluid drainage device comprising a container including a drainage collection chamber in a lower portion thereof, and means forming a removable liquid seal chamber above and extending downwardly into said collection chamber, said liquid seal chamber including a closed sidewall and a bottom wall separating the collection chamber and the liquid seal chamber, a first passage means extending through said bottom wall and open at the upper and lower ends thereof, said first passage means extending upwardly a predetermined distance above said bottom wall, and second passage means for fluid communication with a patient and extending downwardly in the liquid seal chamber to a location below the upper end of the first passage means, and baffle means in the liquid seal chamber in the space between the first and second passage means.

36. The device of claim 35 wherein at least a portion of the baffle means is coated with an anti-foam coating substance.

37. A body fluid drainage device comprising a container including a drainage collection chamber in a lower portion thereof, and means forming a removable liquid seal chamber above and extending downwardly into said collection chamber, said liquid seal chamber including a closed sidewall and a bottom wall separating the collection chamber and the liquid seal chamber, a first passage means extending through said bottom wall and open at the upper and lower ends thereof, said first passage means extending upwardly a predetermined distance above said bottom wall, and second passage means for fluid communication with a patient and extending downwardly in the liquid seal chamber to a location below the upper end of the first passage means, the first passage means having a larger cross-section than the second passage means, the upper end of the first passage means controlling the depth of liquid maintained in the liquid seal chamber, and liquid flow passage means in the liquid seal chamber between the first and second passage means below the upper end of the first passage means, said liquid flow pasage means having substantially greater flow capacity than the flow capacity through the second passage means.

38. The body fluid drainage device of claim 37 wherein the liquid flow passage means includes baffle means separating the liquid seal chamber into chamber portions on opposite sides thereof, said baffle means having an opening therethrough of greater cross-section than the cross-section of the second passage means.

* * * * *